United States Patent [19]

Hanson et al.

[11] 4,346,698

[45] * Aug. 31, 1982

[54] BALLOON CATHETER WITH ROTATABLE SUPPORT

[75] Inventors: Bruce L. Hanson, Wayne, N.J.; Sidney Wolvek, Brooklyn, N.Y.

[73] Assignee: Datascope Corp., Oakland, N.J.

[ * ] Notice: The portion of the term of this patent subsequent to Apr. 14, 1998, has been disclaimed.

[21] Appl. No.: 151,611

[22] Filed: May 20, 1980

Related U.S. Application Data

[63] Continuation-in-part of Ser. No. 883,513, Mar. 6, 1978, Pat. No. 4,261,339.

[30] Foreign Application Priority Data

Sep. 4, 1979 [GB] United Kingdom ............... 7912427

[51] Int. Cl.³ ............................................. A61M 29/02
[52] U.S. Cl. .................................. 128/1 D; 128/344; 128/349 B; 128/DIG. 16
[58] Field of Search ............... 128/1 D, 246, 325, 344, 128/348–351, 347, 214.4, DIG. 16

[56] References Cited

U.S. PATENT DOCUMENTS

| 3,504,662 | 4/1970 | Jones | 128/344 |
| 3,692,018 | 9/1972 | Goetz et al. | 128/344 |
| 3,837,347 | 9/1974 | Tower | 128/344 |
| 3,877,838 | 4/1975 | Choy | 128/344 |
| 3,900,033 | 8/1975 | Leninger et al. | 128/344 |
| 3,939,820 | 2/1976 | Grayzel | 128/344 |
| 3,978,863 | 9/1976 | Fettel et al. | 128/349 B |
| 4,261,339 | 4/1981 | Hanson et al. | 128/348 X |

FOREIGN PATENT DOCUMENTS

| 2456980 | 6/1976 | Fed. Rep. of Germany | 128/349 R |
| 955490 | 4/1964 | United Kingdom | 128/349 R |

Primary Examiner—Stephen C. Pellegrino
Attorney, Agent, or Firm—Darby & Darby

[57] ABSTRACT

An inflatable and deflatable balloon catheter is disclosed. The inflatable chamber of the catheter is supported about an elongated support member of small diameter. One or both ends of the support member are rotatably disposed relative to the chamber wherein the chamber is adapted to being compactly twisted about the support member upon twisting, rolling or wrapping the chamber. The compactly twisted chamber has a small diameter whereby insertion of the catheter through a small incision and guiding thereof in a small body canal or passage is facilitated. A smooth-walled sheath of low friction material is disclosed for enclosing the twisted chamber to facilitate atraumatic entry of the catheter into the incision or body opening and for facilitating insertion and movement of the catheter. Balloon catheters according the present invention are advantageously used for intra-aortic balloon pumping.

9 Claims, 10 Drawing Figures

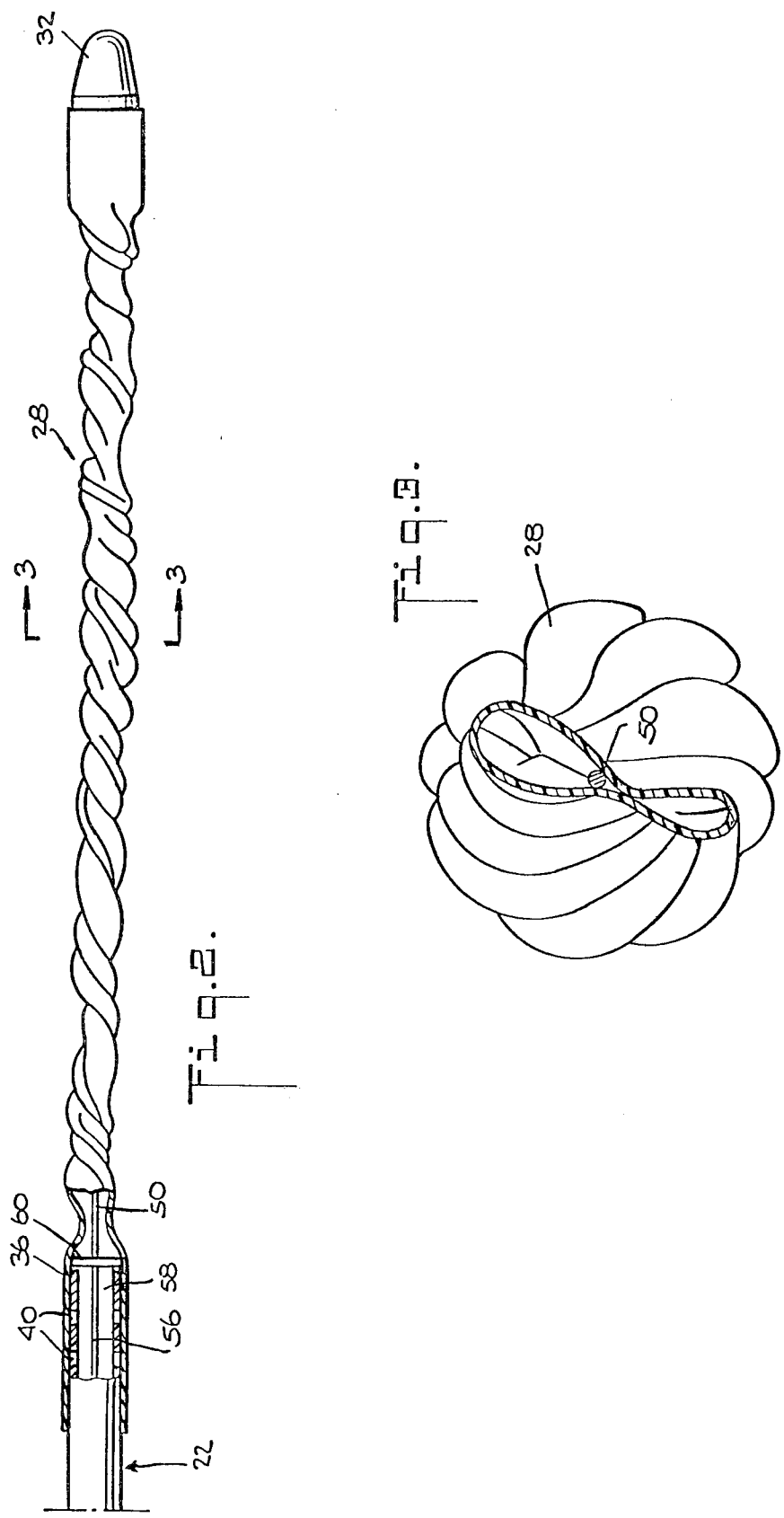

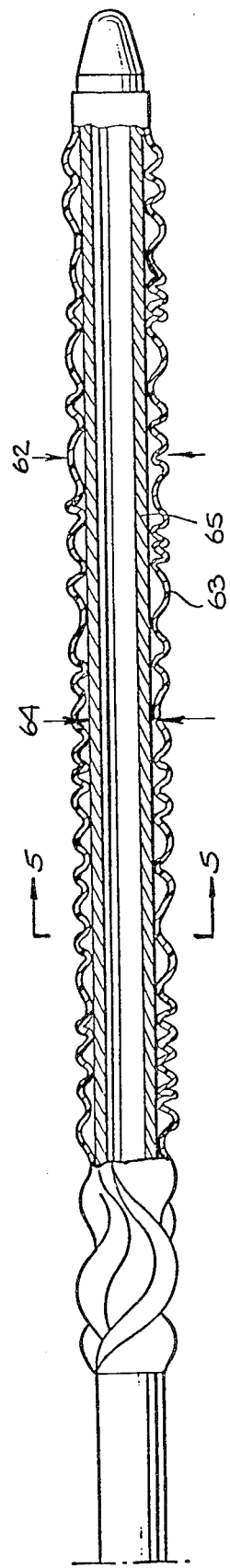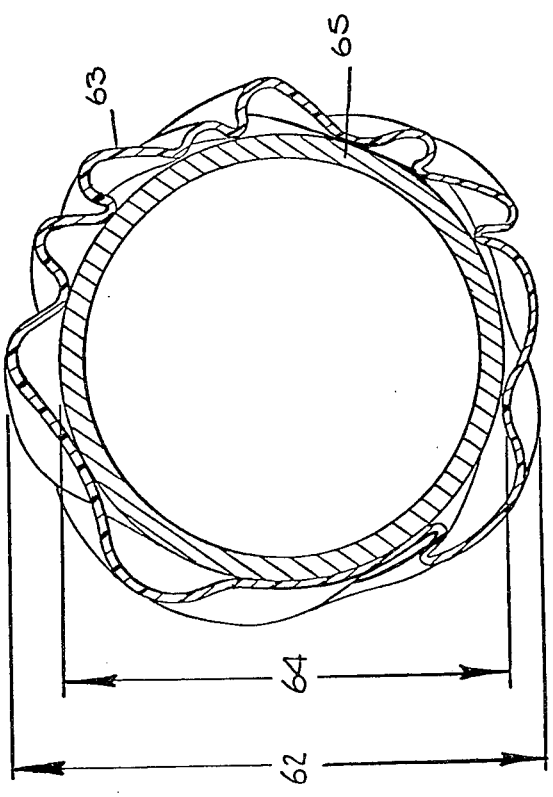

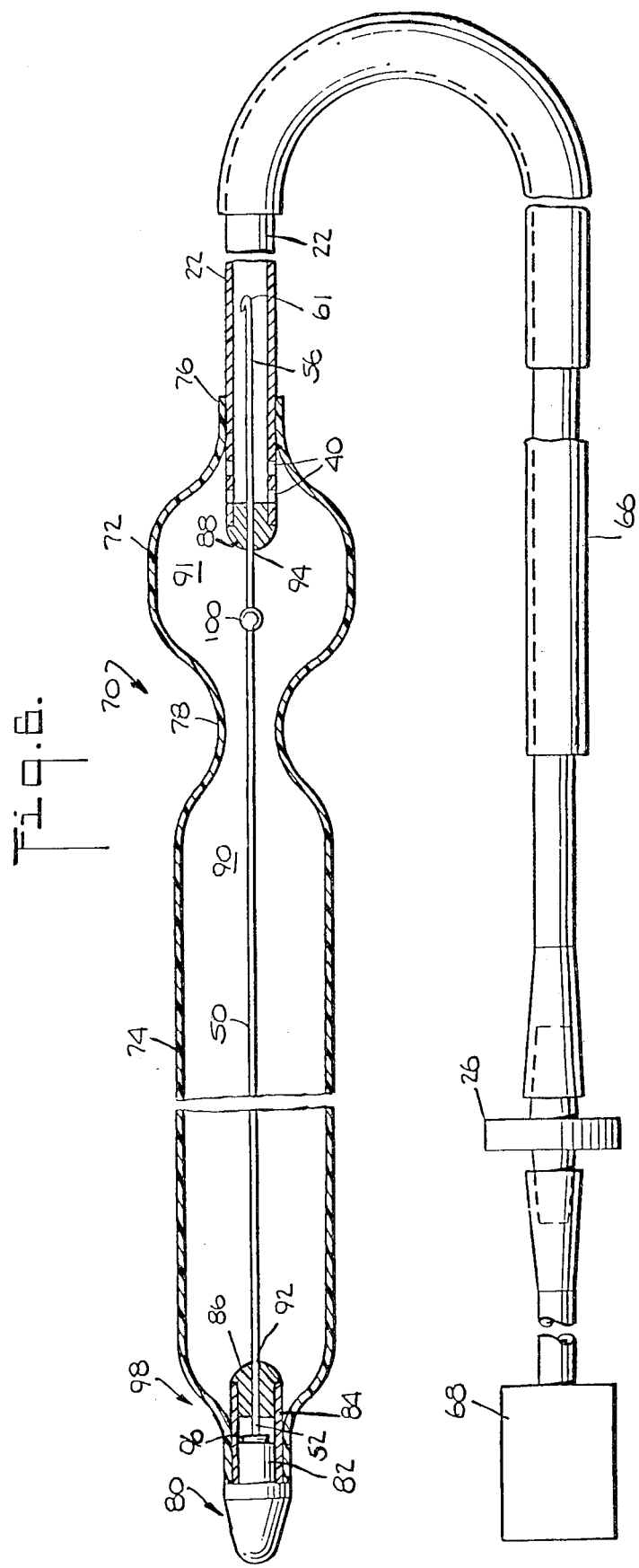

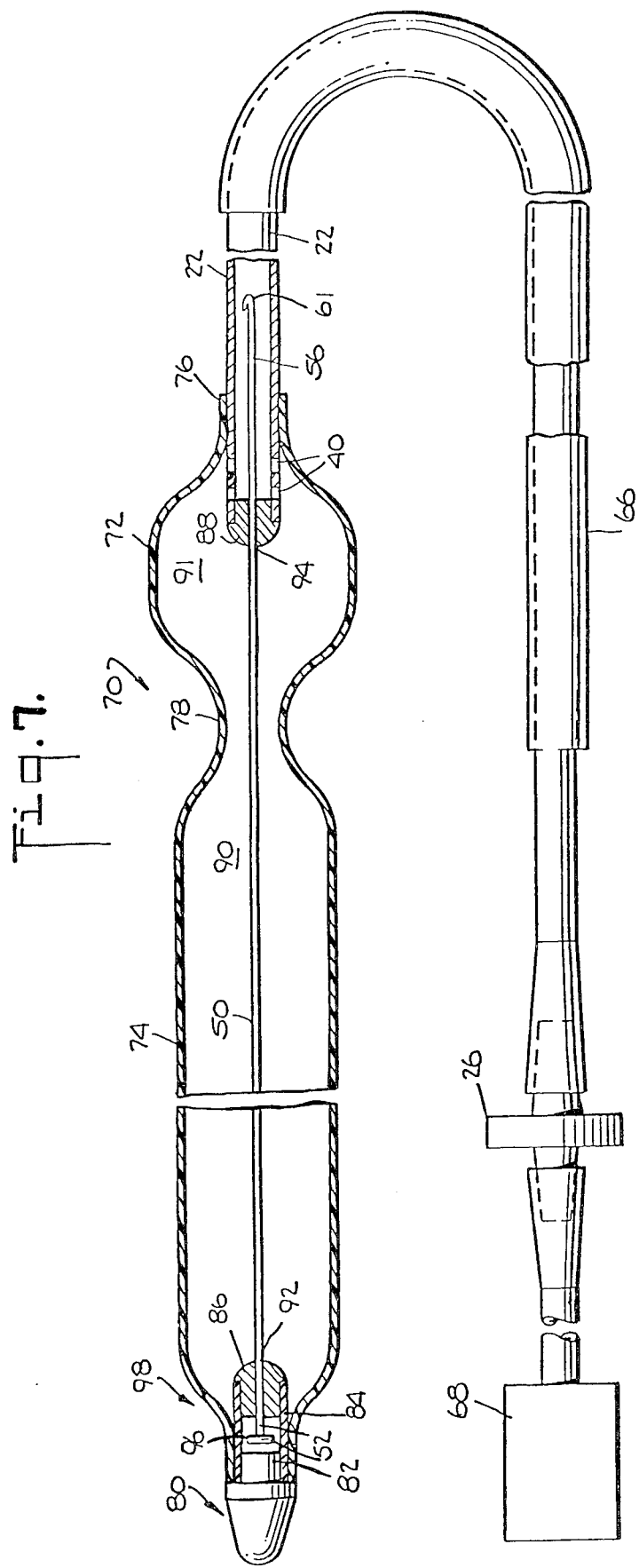

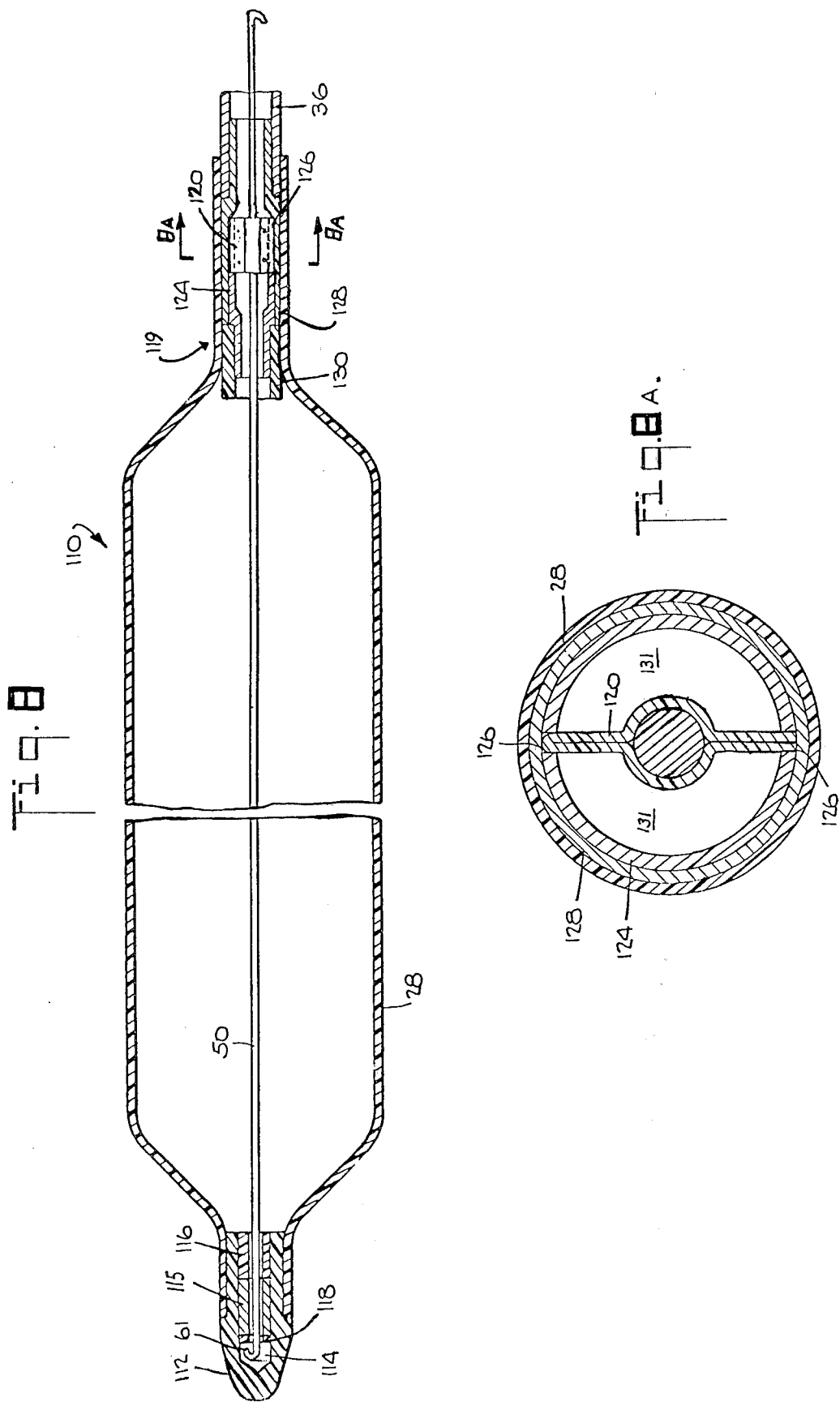

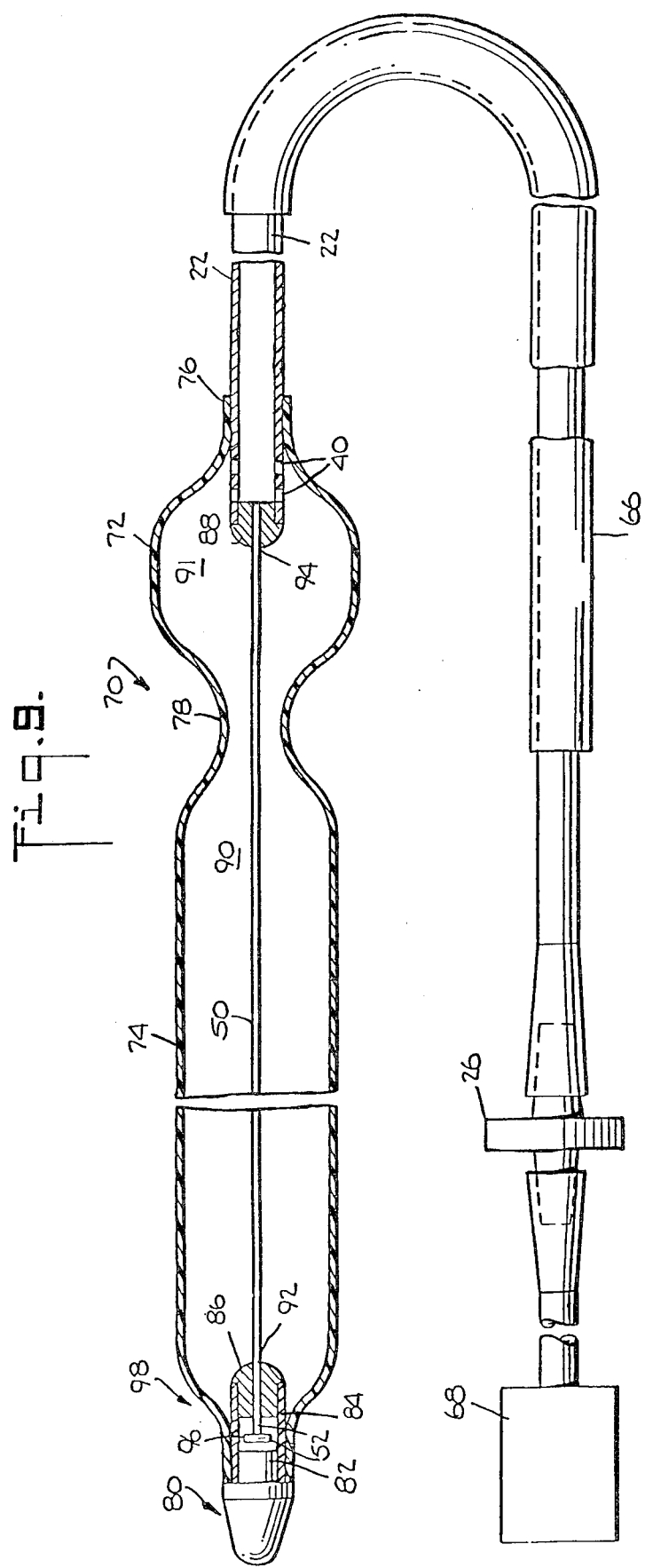

BALLOON CATHETER WITH ROTATABLE SUPPORT

RELATED APPLICATION

This application is a continuation-in-part of our copending application Ser. No. 883,513, filed Mar. 6, 1978, now U.S. Pat. No. 4,261,339, which is assigned to the same assignee.

BACKGROUND OF THE INVENTION

1. Field of the Invention

The present invention relates to catheters and more particularly to an inflatable balloon catheter, particularly for use in intra-aortic pumping.

2. Description of the Prior Art

Intra-aortic balloon pumping is a recognized method of cardiac assistance for a failing heart. It is also a recognized method of treating cardiogenic shock and has been used to help wean a patient way from cardiopulmonary bypass, to support a patient during a difficult postoperative period, and to provide a pulsatile flow to the linear flow supplied by the cardiopulmonary bypass device. Intra-aortic balloon pumping has also been used therapeutically after myocardial infarction to limit the extension of necrosis and has been used as a therapy for angina pectoris.

Catheters for intra-aortic balloon pumping presently utilize a nonstressed or nondistensible balloon, i.e., the balloon is not stretched during inflation and never changes its surface area substantially, inflating and deflating with a predetermined volume of appropriate fluid to achieve phasic operation; the balloon surface area is always substantially equal to that of a fully inflated balloon. The intra-aortic balloon catheters of the prior art are relatively stiff and bulky and have a large "entering" cross-section. The femoral artery has heretofore been used for insertion of these stiff and bulky intra-aortic balloon catheters because of the large diameter of that artery. However, considerable surgery must be performed in order to reach and isolate the femoral artery. In addition, a large incision must be made in the femoral artery wall to permit introduction of these prior art devices. The safeness of intra-aortic balloon pumping using the catherters of the prior art has been questioned since they can cause and in some instances have caused aortic dissections, perforations and trauma mainly because of the entering size and the relative stiffness of the devices. Additionally, this stiffness prevents precise maneuverability of the catheter within the vascular structure and thereby limits its potential for efficacy.

It is recognized in the prior art that insertion and guiding of catheters is difficult and that trauma and damage to the incision and blood vessel may occur during said insertion and guiding. The balloon of prior art catheters is commonly rolled or spirally wrapped around its underlying catheter tube in order to insert it into and guide it in a blood vessel. In Grayzel, U.S. Pat. No. 3,939,820, an attempt is made to obtain a tight wrap in which the size of the enclosed catheter tube is decreased by replacing it with a thin support member or wire. The balloon membrane, however, must still be wrapped, or rolled, and the limited amount of balloon material available and the limited magnitude of the torsional stress that may be applied to twist the balloon limit the tightness of the roll regardless of whether the balloon is twisted around a catheter tube or around a thin support member. In catheters of the prior art, the balloon tip and gas supply tube are rigidly connected to each other within the balloon (Goetz, et al., U.S. Pat. No. 3,692,018 and Jones, U.S. Pat. No. 3,504,662), or are rigidly connected to each other by a thin support member within the balloon (Grayzel, U.S. Pat. No. 3,939,820), or are connected to each other within the balloon by a non-twistable, copper current-carrying braid (Kantrowitz, et al., U.S. Pat. No. 3,585,983). The twisting of the balloon about its longitudinal axis is therefore limited since no rotational displacement is possible between the balloon tip rigidly fastened to the distal end of the balloon and the catheter tube or support means rigidly fastened to the proximal end of the balloon.

SUMMARY OF THE INVENTION

In accordance with the present invention, a new and improved catheter is provided in which the chamber or inflatable balloon of the catheter may be tightly twisted into a small cross-sectional diameter. A smaller entering diameter for the catheter may thereby be obtained enabling the catheter to be inserted into small incisions and body openings and guided through smaller and more tortuous canals and passageways.

It is an object of the present invention to provide a new and improved catheter.

It is also an object of the present invention to provide a catheter capable of being configured into a cross section no larger than that of the inflating gas supply tube of the catheter.

It is an object of the present invention to provide a catheter which may be inserted through small incisions or even by percutaneous insertion.

It is another object of the present invention to provide a catheter having a chamber and support means therefore which are relatively rotatable.

It is still another object of the present invention to provide a catheter incorporating a sheath facilitating atraumatic insertion of the catheter into blood vessels or body openings.

It is another object of the present invention to provide single and multi-chambered catheters embodying the aforementioned objects.

In accordance with the invention, the chamber of the catheter is supported about support means, which the chamber and support means being relatively rotatably disposed. Thus, angular movement is possible between the support means and the chamber in the preferred embodiments, one or both ends of the support means are rotatable relative to the chamber wherein the chamber is adapted to being compactly wrapped, rolled or twisted about the support means upon rotation of the chamber. The support means is of small diameter and is disposed within the chamber. In one embodiment, the support means is connected with the chamber at one end thereof and rotatable with respect to the remainder of the catheter at the other end of the chamber whereby the support means may be rotated or swiveled relative to the catheter. In another embodiment, the support member is rotatably mounted with respect to both ends of the chamber. Rotatable disposition of the support means in the catheter chamber permits tight twisting of the chamber about the support means without distorting or damaging the conduit means for transmitting fluid into and out of the chamber. Thus, the torque applied to the chamber in twisting it is not imparted to the conduit means and the remainder of the catheter.

A catheter according to the disclosing embodiments of the invention comprises gas supply means for transmitting gas into and out of the balloon and an elongated, rod-like support member in the balloon for supporting the balloon, the proximal end of the balloon being non-rotatably connected to the gas supply means and the balloon being rotatably secured to the support member. Means are provided to prevent the support member from telescoping or collapsing as the catheter is inserted and guided during use. The balloon is wrapped about the support member by rotation of the proximal or the distal end of the balloon.

In accordance with another aspect of the invention, a sheath is provided to enclose the balloon in the wrapped configuration thereof. The sheath is thin-walled, smooth and has a low coefficient of friction to thereby facilitate entry and guiding of the catheter and to reduce trauma.

Smaller entering diameters and controllability of catheters according to the invention, combined with the ease of insertion, makes it possible to insert such catheters into smaller and more accessible arteries than the femoral artery, for example, the brachial or the axillary artery. Intra-aortic balloon pumping can be carried out with catheters according to the invention without undergoing the extensive surgery of a femoral arteriotomy and therefore may become available to many more patients. Those patients for whom the standard transfemoral approach is impossible because of atheromatous femoral arteries, obstructive aortoiliac disease, or a contaminated or previously cannulated groin may now be treated by the more easily inserted and more flexible catheters of the invention.

It is therefore contemplated that the catheters according to the present invention will make intra-aortic balloon pumping available to many more people than can now be treated by the use of the relatively stiff, bulky prior art balloon catheters and the obligatory use of the femoral arteries because of the large "entering" bulk of the prior art catheters.

It is also within the contemplation of the present invention that the catheters of the invention be percutaneously insertable, i.e., insertable through the skin without surgery.

These and other aspects of the invention will be more apparent from the following description of the preferred embodiments thereof when considered with the accompanying drawings and appended claims.

BRIEF DESCRIPTION OF THE DRAWINGS

The present invention is illustrated by way of example and not limitation in the figures of the accompanying drawings in which like references indicate similar parts and in which:

FIG. 2 is a side view, partly in section, showing the balloon of the catheter of FIG. 1 in its twisted or wrapped configuration;

FIG. 3 is a section view taken along 3—3 of FIG. 2;

FIG. 4 is a side view, partly in section, of a prior art catheter showing the balloon thereof in a rolled or twisted configuration;

FIG. 5 is a section-view taken along lines 5—5 of the prior art catheter of FIG. 4;

FIG. 6 is a side view, partly in section, of a dual-chamber catheter according to another embodiment of the inventor;

FIG. 7 is a side view similar to FIG. 6 showing a further embodiment of the invention in which the chamber is rotatably mounted to both ends of the chamber;

FIG. 8 is a sectional view of the balloon portion of a balloon catheter according to another embodiment of the invention in which the support means are rotatably mounted with respect to both ends of the chamber;

FIG. 8A is a section-view taken along line 8—8A of FIG. 8; and

FIG. 9 is a side view of a device in which the support member is rotatably secured to the tip and non-rotatably secured to the catheter tube.

DESCRIPTION

Figure 1:
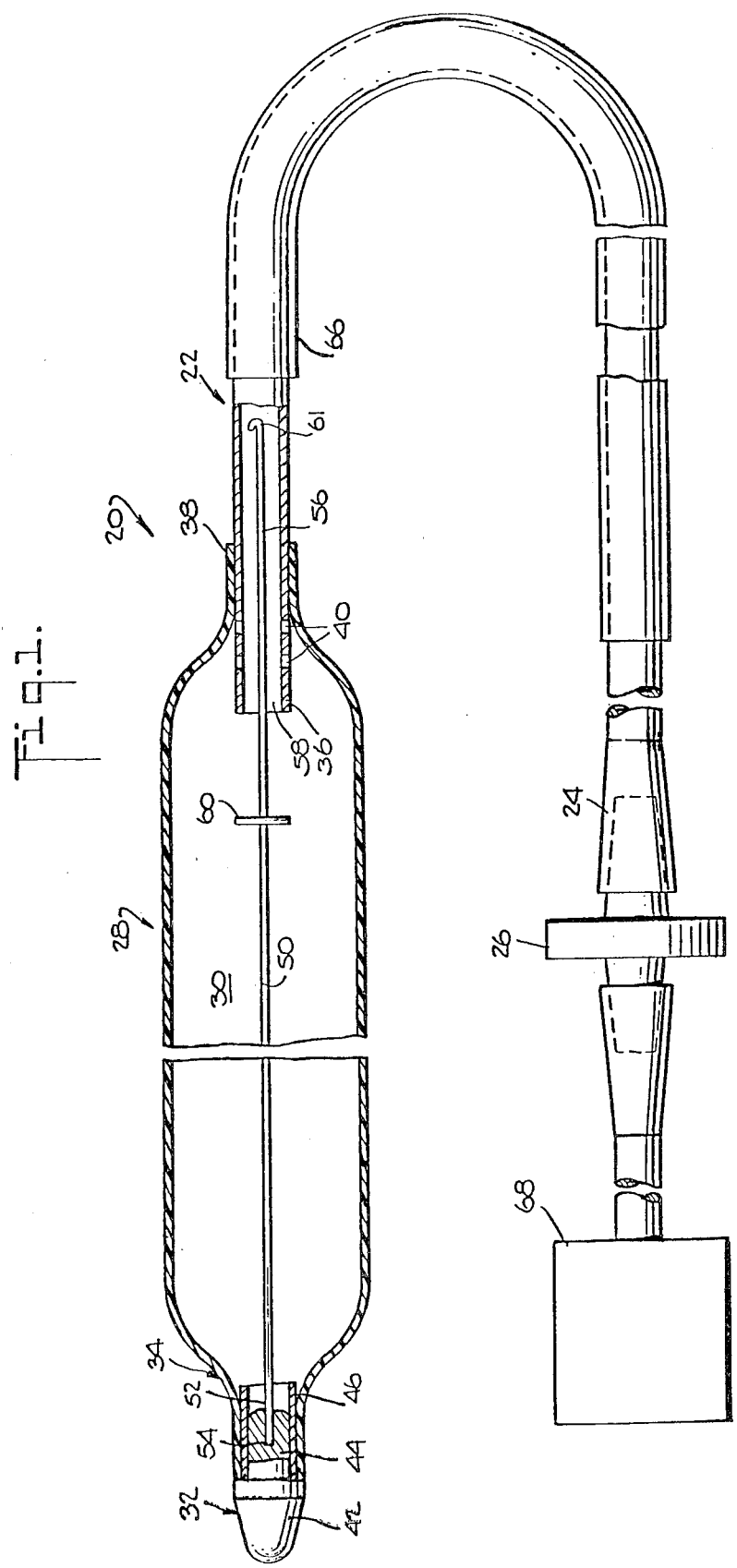
FIG. 1 is a side view, partly in section, of the catheter according to the invention showing the balloon thereof in an untwisted configuration.

As shown in FIG. 1, catheter 20 according to the invention includes a hollow, flexible catheter gas supply tube 22 affixed at one end 24 thereof to connector 26 and adjacent the other end thereof to an elastomeric balloon 28. Catheter 20 is an omnidirectional intra-aortic balloon catheter and includes the single balloon chamber 30. In accordance with the preferred embodiments illustrating the invention and not by way of limitation, the balloon is not stressed during inflation and deflation, i.e., the balloon material is non-distensible and has substantially the same surface area when inflated and when deflated. A rigid tip 32 is fluid-tightly affixed to the distal end 34 of the balloon. The gas supply tube 22 terminates in end 36 adjacent proximal end 38 of the balloon 28 which is disposed within chamber 30 of the balloon 28 a small distance sufficient to accomodate within chamber 30 a plurality of gas supply tube 22. The gas ports 40 communicate the interior of the gas supply tube with chamber 30. The proximal end 38 of the balloon is fluid-tightly bonded circumferentially to gas supply tube 22 and the distal end 34 of the balloon is fluid-tightly bonded circumferentially to tip 32 by, for example, an adhesive or by welding. The tip, balloon and gas supply tube are coextensive at least in part to form a continuous member having good flexibility at the junction of the tip and balloon and the gas supply tube and balloon.

Tip 32 includes an end portion 42 having a section 44 of reduced diameter and a sleeve 46. The sleeve is fluid-tightly circumferentially bonded about section 44 and the balloon end is fluid-tightly circumferentially bonded to the sleeve by, for example, an adhesive or by welding. The parts of tip 32, sleeve 46 and tube 22 within chamber 30 are smoothly contoured to reduce stress and wear on the balloon during operation thereby preventing puncturing, cutting or rupturing of the balloon.

Interposed between tip 32 and tube 22 in chamber 30 is support wire 50. End 52 of the support wire is nonrotatably secured in hole 54 of tip 32 and end 56 is rotatably disposed in opening 58 of tube end 36. End 52 extends into tip 32 and is soldered therein or non-rotatably affixed therein by other means such as adhesives, for example. End 52 abuts against the end of hole 54 and together with the non-rotatable affixing of end 52 to tip 32 prevents movement of wire 50 towards the distal end 34 of the balloon. A disc-shaped keeper 60 secured to the wire 50 adjacent tube end 36 prevents movement of the wire toward the proximal end 38 of the balloon and prevents the wire from being forced further into the end of tube 22 when pressure is applied to the balloon during insertion of the catheter. Opening 58 permits wire 50 to rotate freely therein. The end 56 of the wire extends sufficiently into tube 22 to prevent the wire from being withdrawn through opening 58. Wire end 56 at the extremity 61 thereof is rounded to prevent damage to the wall of tube 22.

In accordance with the invention, the provision of the thin support wire 50 rotatably disposed in the gas supply tube permits the support wire to be rotated or swiveled relative to the gas supply tube, thereby permitting the balloon to be easily and compactly twisted about the support wire. This results in the twisted balloon having a smaller cross-sectional area which approaches that of tip 32 and gas supply tube 22. Thus, the overall cross-sectional area of catheter 20 may be reduced for insertion into smaller incisions. Additionally, the torque applied to twist the balloon during wrapping thereof is not imparted to the gas supply tube thereby preventing stress to and damage of the gas supply tube.

In use, balloon tip 32 is grasped and rotated to tightly twist balloon 28 about the thin wire support 50. Since the wire may be freely rotated within tube end 36, the tip may be rotated for many revolutions to impart a compact twist to the balloon as shown in FIG. 2. As the balloon is twisted about its own axis, its cross-sectional area is reduced, as shown in FIG. 3, and the cross-sectional area is inversely proportional to the number of rotations of the tip. Thus, the largest cross-sectional diameter of the catheter is that of the twisted balloon which approaches that of tip 32 and gas supply tube 22. A vacuum is applied to the interior of the wound balloon to keep it from unwinding. After insertion when the balloon is in the desired position, the vacuum is removed and the balloon unwinds. In contrast, the much larger cross-sectional configuration of a prior art catheter in which the balloon is wrapped on the interior support or catheter tube is shown in FIGS. 4 and 5. The largest cross-sectional diameter 62 of the unwrapped balloon 63 is considerably larger than the cross-sectional diameter 64 of the catheter tube 65.

After the balloon has been twisted about the support wire as shown in FIGS. 2 and 3, a sheath 66 (FIG. 1) may be slid over the balloon to enclose it and enhance performance of the catheter. However, it is to be understood that the present invention as described above may be practiced without the sheath and that the sheath may be used to enhance performance. The sheath also prevents the balloon from unwinding. When a sheath is used, the vacuum may optionally be applied to the interior of the wound balloon. The sheath 66 is thin-walled and made of a low friction flexible material such as Teflon, Mylar or polyethylene. When used, it is positioned on the gas supply tube 22 adjacent the balloon 28 (FIG. 1) prior to its being drawn over the twisted balloon. In addition to locking the balloon in its twisted configuration, the sheath is smooth-walled and, as mentioned, is made of low friction material to facilitate insertion of the catheter. Sheath 66 is sufficiently long so that a portion thereof remains exposed after the catheter has been advanced to the desired location. The exposed portion is used to withdraw the sheath from over the twisted balloon and return it to its position on the gas supply tube 22. The balloon will then unwind due to the elastomeric nature of the balloon material and the inflating gas pressure. The sheath facilitates atraumatic entry of the catheter into the incision and blood vessel and facilitates insertion and guiding of the catheter in the blood vessel, however, as mentioned, use of the sheath is not mandatory.

A gas supply source 68 is connected to the catheter by means of the connector 26 and supplies and withdraws gas to the gas chamber 30 through gas supply tube 22 to achieve phasic operation of the catheter for the intra-aortic balloon pumping procedure.

The present invention may be embodied in dual or multi-chamber catheters in addition to the single chamber catheter described hereinbefore. Referring to FIG. 6, dual-chamber catheter 70 includes a second or occluding balloon section 72 in addition to the pumping balloon section 74 similar to balloon 28 of FIG. 1. Occluding balloon section 72 is bonded to tube 22 at end 76 of the balloon as described for balloon 28. The neck 78 between the balloon sections insures that the occluding balloon 72 is inflated before the pumping balloon 74 is inflated, thereby insuring optimal unidirectional balloon pumping action. It is understood, however, that the position of the occluding balloon 72 may be other than between balloon 74 and connector 26. In some instances, unidirectional pumping is more efficacious if the occluding balloon 72 is placed between tip 32 and the pumping balloon as shown in FIG. 3 of Grayzel, U.S. Pat. No. 3,939,820. While a single balloon is shown which forms separate balloon chambers, the multi-chambered catheter may comprise separate balloons. The distal tip and proximal end of the catheter tube may be configured as shown and described for the balloon catheter of FIG. 1. Alternatively, a rigid tip 80 may be provided having a section 82 of reduced diameter, a sleeve 84 and a plug 86. The sleeve is fluid-tightly circumferentially bonded about section 82 and the balloon end is fluid tightly circumferentially bonded to the sleeve by, for example, an adhesive or by welding. The parts of tip 80 and tube 22 including plugs 86 and 88 within the chambers are smoothly contoured to reduce stress and wear on the balloon during operation thereby preventing puncturing, cutting or rupturing of the balloon.

Interposed between tip 80 and tube 22 in chambers 90, 91 is the support wire 50. End 52 of the support wire is nonrotatably secured in hole 92 of plug 86 and end 56 is rotatably disposed in hole 94 of plug 88. A disc 96 is soldered to the end 52 of the wire which protrudes through plug 86, the disc abutting against section 82 of tip 80. This, together with the securing of the wire within hole 92 by means of, for example, an adhesive, prevents movement of wire 50 towards the distal end 98 of the balloon. Wire 50 includes a section 100 of enlarged diameter adjacent plug 88 which prevents movement of the wire toward the proximal end 76 of the balloon and prevents the wire from being forced further into the plug and tube 22 when pressure is applied to the balloon tip during insertion of the catheter. Hole 94 is sized to permit wire 50 to rotate freely therein. Section 100 is shown to be a spherically-shaped keeper, however, other shapes will also be suitable. The end 56 of the wire extends sufficiently into tube 22 to prevent the wire from being withdrawn through hole 94 of plug 88. Wire end 56 at the extremity 61 thereof is rounded to prevent damage to the wall of tube 22, as described for the catheter shown in FIG. 1.

The catheters according to the invention are fabricated of biologically acceptable material. The tube 22 is formed, for example, of polyurethane. Tip 32 is formed, for example, from stainless steel or Lexan and the connector, from polyethylene or polypropylene. Balloon 28 (72, 74) is made, for example, of a thin film of polyurethane. Other biologically acceptable materials may also be used. Gases such as air, carbon dioxide and helium or liquids are used to inflate the catheter when used for intra-aortic balloon pumping.

While the invention has been heretofore illustrated with the support wire rotatable relative to the gas supply tube and nonrotatably connected to the distal tip, it is to be understood that it is contemplated according to the invention that the support wire may be rotatably secured to the distal tip and nonrotatably connected to the gas supply tube. This is shown in FIG. 9, described below.

The support member may be rotatably mounted to the distal tip and the gas supply tube, as shown in FIG. 7 and also made rotatable relative to the gas supply tube 22. In the device of FIG. 7, the bore 92 of the plug 86 through which support wire 50 passes is made sufficiently large so that the support wire can rotate therein. Also, the section 82 has been shortened from that of FIG. 2 and the head 96 of the support wire is free to rotate in the space between plug 84 and the section 82. The head 96 limits the travel of the support 50 to a distance between the plug 84 and the section 82. As before, the support 50 is free to rotate in the hole 94 in the plug 88 at the catheter end. Thus, the support member can be rotated relative to the catheter tube end and the balloon rotated relative to the support member at the tip end. If the balloon is rotated at the tip end, there is a free wrapping action about the support member due to the double rotation mounting and, therefore, a free action during unwrapping.

While the embodiment of FIG. 7 is similar in configuration to that of FIG. 6, it should be understood that other types and shapes of chambers can be used, for example, the single chamber device of FIG. 1. An arrangement for this is shown in FIGS. 8-8A.

FIGS. 8-8A show a single chamber balloon embodiment. Catheter 110 includes a tip 112 which has a hollow portion 114 therein. Disposed in the hollow portion are annular sleeves 115, 116. Sleeve 116 is bonded to tip 112 as described for sleeve 46 and tip 32, and acts as a keeper to maintain sleeve 115 which may be of stainless steel in hollow portion 114. The support wire 50 extends through the central opening in the annular sleeves 115 and 116 and clearance is provided so that the wire is freely rotatable with respect to the sleeves. The support wire 50 extends past the sleeves and terminates in a rounded section 61 in the hollow portion of the tip 112. A washer 118 is disposed adjacent the sleeve 114.

At the proximal end of the chamber, the support wire 50 is made rotatable relative to the catheter tube portion 36 by means of, for example, an assembly 119 in which support member 50 is located. Assembly 119 includes ribbon 120 which comprises a stainless steel sheet-like element which is folded over and spot welded to provide a central opening in which the support wire is disposed and in which it can freely rotate. The ribbon 120 is non-rotatably disposed in inner stainless steel sleeve 124 with the ribbon ends being received in opposed axial slots 126 in sleeve 124. The part of the inner sleeve including the axial slots is disposed in and spot welded to an outer stainless steel sleeve 128 which in turn is bonded fluid-tightly to the balloon 28 and to the catheter tube end 36. The remaining part of the inner sleeve is disposed in and bonded to another sleeve 130 which in turn is bonded fluid-tightly to balloon 28. Use of the relatively thin ribbon provides relatively large spaces 131 between the ribbon and the inner sleeve for the fluid to flow into and and out of the balloon chamber. As described with respect to FIG. 8, the tip of the chamber is rotatable relative to the support means and the support means is rotatable relative to the end of the catheter tube.

The mounting arrangement at the end of the catheter tube 119 can be used in an embodiment where the tip of the chamber is non-rotatably attached to the support member. As seen in FIG. 8, this mounting arrangement has the advantage of a good flow for the fluid past the ribbon 120. Also, the sleeve 130, extends into the chamber for a shorter distance than, for example, element 36 in FIG. 1 and the fluid escape ports 40 are not used, allowing a tighter wrap of the balloon at the proximal end.

In FIG. 9, which is similar to FIG. 7, there is shown a device wherein the end of the support member 50 is rotatable in the plug 86 at the tip end previously described. Here, however, the end of the support member is fixed to plug 88 in the catheter tube portion, so that it will not rotate.

The advantages of the present invention, as well as certain changes and modifications of the disclosed embodiments thereof, will be readily apparent to those skilled in the art. It is the applicants' intention to cover by their claims all those changes and modifications which could be made to the embodiments of the invention herein chosen for the purpose of the disclosure without departing from the spirit and scope of the invention. Protection by Letters Patent of this invention in all its aspects as the same are set forth in the appended claims is sought to the broadest extent that the prior art allows.

We claim:

1. A catheter comprising an inflatable and deflatable chamber having opposed ends, a catheter tube portion, one end of said chamber connected to said catheter tube portion, an elongated support member extending in said chamber between the opposed ends thereof, one end of said support member disposed at said end of said catheter tube portion and the other end disposed at the other end of the chamber opposed from said one end connected to the catheter tube portion, said support member supporting said chamber and being rotatably disposed with respect to each end of said chamber, said chamber being adapted to be rotated relative to said catheter tube portion and to be wrapped about said support member.

2. The catheter of claim 1, wherein the catheter tube portion includes a fluid passage therein in communication with the interior of said chamber and adapted to being communicated with a source of fluid, whereby the chamber may be inflated and deflated.

3. The catheter of claim 2 wherein said catheter tube portion terminates in an opening which communicates with the interior of said chamber and said fluid passage in said catheter tube portion and wherein one end of said support member is rotatably disposed in said opening and the other end of said support member is rotatably connected to said other end of said chamber.

4. The catheter of claim 1 further comprising a tip member disposed at said other end of said chamber, said other end of said chamber terminating at said tip member and being connected fluid-tightly thereto, and wherein said support member is rotatably connected to said tip member.

5. The catheter of claim 4 wherein said support member further comprises means for limiting axial motion of said support member relative to said tip.

6. The catheter of claim 3 further comprising means on said catheter tube portion for rotatably mounting the end of the support means which extends within the catheter opening.

7. The catheter as in claim 6 wherein said mounting means comprises a ribbon type connector which permits the flow of fluid through the fluid passage of said catheter tube portion.

8. The catheter of claim 1 wherein said one end of said support member extends within said catheter tube portion.

9. The catheter of claim 8 wherein one end of said catheter tube portion terminates adjacent said one end of said chamber.

* * * * *